US009827019B2

United States Patent
Guitao (10) Patent No.: US 9,827,019 B2
(45) Date of Patent: Nov. 28, 2017

(54) RETURNABLE AND DYNAMIC FIXATION PEDICLE SCREW SYSTEM OF RAIL-CHAIN TYPE FOR SOCKET

(71) Applicants: Wei Yuanfang, Guangdong Province P.R. (CN); GUANGDONG NO. 2 PROVICIAL PEOPLE'S HOSPITAL, Guangdong Province P.R. (CN)

(72) Inventor: Li Guitao, Guangzhou (CN)

(73) Assignees: Wei Yuanfang, Guangdong Province (CN); Guangdong No. 2 Provicial People's Hospital, Guangdong Priovince (CN)

( * ) Notice: Subject to any disclaimer, the term of this patent is extended or adjusted under 35 U.S.C. 154(b) by 0 days.

(21) Appl. No.: 14/969,090

(22) Filed: Dec. 15, 2015

(65) Prior Publication Data

US 2016/0296257 A1    Oct. 13, 2016

(30) Foreign Application Priority Data

Apr. 13, 2015  (CN) .......................... 2015 1 0173832

(51) Int. Cl.
*A61B 17/70*    (2006.01)
(52) U.S. Cl.
CPC ................................ *A61B 17/7037* (2013.01)
(58) Field of Classification Search
CPC .................................... A61B 17/7032–17/7046
See application file for complete search history.

(56) References Cited

U.S. PATENT DOCUMENTS

| 5,466,237 | A | * | 11/1995 | Byrd, III | A61B 17/7037 606/272 |
| 5,733,286 | A | * | 3/1998 | Errico | A61B 17/7037 606/266 |
| 5,782,833 | A | * | 7/1998 | Haider | A61B 17/7037 606/266 |
| 6,443,953 | B1 | * | 9/2002 | Perra | A61B 17/7032 606/270 |
| 6,485,491 | B1 | * | 11/2002 | Farris | A61B 17/7002 606/250 |
| 6,554,834 | B1 | * | 4/2003 | Crozet | A61B 17/7082 606/272 |
| 7,695,497 | B2 | * | 4/2010 | Cordaro | A61B 17/7032 606/266 |

(Continued)

*Primary Examiner* — Eduardo C Robert
*Assistant Examiner* — Michelle C Eckman
(74) *Attorney, Agent, or Firm* — Verrill Dana, LLP; John W. Powell (57) ABSTRACT

A socket rail pedicle screw includes a fixator, a spherical head screw pivotally disposed at a bottom of the fixator and a retention screw cap. The fixator has a circular sidewall and a though hole. A pair of U-shaped grooves is defined on a top portion of the circular sidewall and a pair of locating steps is internally extended from an inner wall of a bottom portion of the circular sidewall and below the U-shaped grooves. The spherical head screw includes a bolt and a pair of diametrically faced socket rails. Each socket rail is constructed by a second top wall and a corresponding second sidewall extended from the second top wall to the bottom of the head. The second top wall is vertically pressed against the first top wall, both of the first and second sidewalls are arced, and a gap is defined between the first and second sidewall.

12 Claims, 7 Drawing Sheets

(56) References Cited

U.S. PATENT DOCUMENTS

| | | | | |
|---|---|---|---|---|
| 8,906,068 B1* | 12/2014 | Bedor | A61B 17/7037 | 606/267 |
| 8,951,294 B2* | 2/2015 | Gennari | A61B 17/7037 | 606/266 |
| 9,084,634 B1* | 7/2015 | Lab | A61B 17/7038 | |
| 2001/0001119 A1* | 5/2001 | Lombardo | A61B 17/7037 | 606/264 |
| 2001/0012937 A1* | 8/2001 | Schaffler-Wachter | A61B 17/7037 | 606/266 |
| 2002/0022842 A1* | 2/2002 | Horvath | A61B 17/7032 | 606/302 |
| 2003/0055426 A1* | 3/2003 | Carbone | A61B 17/7034 | 606/271 |
| 2004/0225289 A1* | 11/2004 | Biedermann | A61B 17/8605 | 606/257 |
| 2005/0216003 A1* | 9/2005 | Biedermann | A61B 17/7032 | 606/279 |
| 2006/0079895 A1* | 4/2006 | McLeer | A61B 17/863 | 606/279 |
| 2006/0111715 A1* | 5/2006 | Jackson | A61B 17/861 | 128/897 |
| 2007/0090238 A1* | 4/2007 | Justis | A61B 17/7038 | 248/181.1 |
| 2007/0118123 A1* | 5/2007 | Strausbaugh | A61B 17/7032 | 606/272 |
| 2007/0233080 A1* | 10/2007 | Na | A61B 17/7032 | 606/278 |
| 2008/0177260 A1* | 7/2008 | McKinley | A61B 17/7038 | 606/60 |
| 2009/0076552 A1* | 3/2009 | Tornier | A61B 17/7038 | 606/264 |
| 2010/0094343 A1* | 4/2010 | Pham | A61B 17/7038 | 606/246 |
| 2010/0241170 A1* | 9/2010 | Cammisa | A61B 17/7032 | 606/264 |
| 2011/0040338 A1* | 2/2011 | Jackson | A61B 17/7032 | 606/305 |
| 2011/0106173 A1* | 5/2011 | Lindemann | A61B 17/7037 | 606/302 |
| 2011/0106174 A1* | 5/2011 | Rezach | A61B 17/7032 | 606/305 |
| 2011/0112578 A1* | 5/2011 | Keiser | A61B 17/7032 | 606/264 |
| 2011/0178558 A1* | 7/2011 | Barry | A61B 17/8605 | 606/302 |
| 2011/0178559 A1* | 7/2011 | Barry | A61B 17/7032 | 606/302 |
| 2011/0257690 A1* | 10/2011 | Rezach | A61B 17/7032 | 606/302 |
| 2011/0282399 A1* | 11/2011 | Jackson | A61B 17/702 | 606/305 |
| 2012/0016425 A1* | 1/2012 | Shaffrey | A61B 17/7032 | 606/305 |
| 2013/0023935 A1* | 1/2013 | Pham | A61B 17/7038 | 606/264 |
| 2013/0150904 A1* | 6/2013 | Biedermann | A61B 17/84 | 606/328 |
| 2013/0211458 A1* | 8/2013 | Rezach | A61B 17/7038 | 606/264 |
| 2014/0214097 A1* | 7/2014 | Jackson | A61B 17/7037 | 606/305 |
| 2015/0127055 A1* | 5/2015 | Dvorak | A61B 17/7038 | 606/279 |
| 2015/0282844 A1* | 10/2015 | Vedula | A61B 17/7032 | 606/305 |
| 2016/0262801 A1* | 9/2016 | Rezach | A61B 17/7032 | |
| 2016/0262803 A1* | 9/2016 | Nelson | A61B 17/7032 | |

* cited by examiner

RETURNABLE AND DYNAMIC FIXATION PEDICLE SCREW SYSTEM OF RAIL-CHAIN TYPE FOR SOCKET

RELATED APPLICATION

This application claims the benefit of the priority date of Chinese Application No. 201510173832.8, filed on Apr. 13, 2015, the contents of which are incorporated herein by reference in its entirety.

FIELD OF THE INVENTION

The present invention relates to technical field of spine fixation using fusion or non-fusion and more particularly, to a pedicle screw for socket and returnable and dynamic fixation pedicle screw system of rail-chain type for socket.

BACKGROUND OF THE INVENTION

Currently all kinds of spine surgical operations should be done in consideration of spine stabilization. To maintain stabilization of spine, an orthopedics-spine surgeon has to employ spine fusion operation, thus losing movement function of the spine segments. However, after spine fusion fixation, it becomes difficult for the patient to bend his neck or waist and the patient feels uncomfortable, because the patient suffers from one disease to another disease. As such, spine fixation by non-fusion to keep certain activity for the spine has been always focused and researched by foreign and domestic spinal surgery.

Pedicle screw system cable of realizing limited spine activity for the post-operative patient is one kind of non-fusion spine fixation technique. Prior art dynamic pedicle screw or dynamic stick non-fusion system has low reliability regarding joint activity of sagittal section and coronal section of the spine segments; and this technique lacks of design and structure for fatigue resistance. Moreover, some screw systems lack of soft transmission of force, lack of shock and vibration resistance.

SUMMARY OF THE INVENTION

The object of the invention is to provide a socket rail pedicle screw and a returnable and dynamic fixation pedicle screw system of rail-chain type for socket capable of resilient and dynamic fixation of the spine of the patient after operation, thus facilitating spine recovery of the patient after operation.

To this end, there is provided the following solution.

A socket rail pedicle screw includes a fixator, a spherical head screw pivotally disposed at a bottom of the fixator, and a retention screw cap pressed against the spherical head screw.

The fixator has a circular sidewall and a though hole defined by the sidewall, a pair of diametrically faced and U-shaped grooves is defined on a top portion of the circular sidewall, a pair of locating steps is internally extended from an inner wall of a bottom portion of the circular sidewall and the pair of steps is located below the pair of U-shaped grooves, and each of the locating steps is formed by a first top wall and a first sidewall collectively.

The spherical head screw includes a bolt and a spherical head disposed at the top portion of the bolt, a pair of diametrically faced socket rails is formed on a lower portion of the head, and each socket rail is constructed collectively by a second top wall and a corresponding second sidewall extended from the second top wall to the bottom of the head.

The second top wall is vertically pressed against the first top wall, both of the first sidewall and second sidewall are arced sidewalls, and a gap is defined between the first sidewall and second sidewall.

To adjust activity range of the spherical head screw, the width of the first sidewall is smaller than that of the second sidewall.

The socket rail may be implemented by the following two manners:

First, the head includes a body which is recessed to form a second top wall and a second sidewall.

Second, the head includes a body which is externally extended to form a second top wall and a second sidewall.

To realize resilient fixation and/or reduce impact during activity, a buffer layer is disposed on both of the first top wall and first sidewall. Or, a buffer layer is disposed on both of the second top wall and second sidewall.

Further, the screw further comprises a resilient filling element disposed inside the fixator.

A returnable and dynamic fixation pedicle screw system of rail-chain type for socket includes a plurality of socket rail pedicle screws as mentioned above and a rectifying rod interconnecting these screws, said rectifying rod being located into the pair of U-shaped grooves of each socket rail pedicle screw.

In addition, the system also includes a resilient filling element disposed inside a corresponding socket rail pedicle screw, said resilient filling element including a supporting cushion placed underneath the rectifying rod and an adjusting cushion disposed above the head of the spherical head screw.

In particular, a notch is defined in the supporting cushion for axial engagement with the rectifying rod.

Optionally, the adjusting cushion is constructed by laminating a plurality of wave-shaped gaskets.

Optionally, the resilient filling element is integrally formed.

Compared to prior art, the invention bears the following good effects.

At first, in the returnable and dynamic fixation pedicle screw system of rail-chain type for socket according to current invention, because of engagement and relative movement between the locating step formed on the inner wall of the fixator and socket rail formed on the head of the spherical head screw, limited adjustment of the spherical head screw is achieved. In addition, this system has simple construction, definite force distribution, stability, safety, is easy to manufacture, and is helpful to recovery of the patient after operation.

Secondly, in the returnable and dynamic fixation pedicle screw system of rail-chain type for socket according to current invention, the resilient filling element is inserted between the rectifying rod and spherical head screw, a pedicle screw system with various adjustment range and resiliency may be made by adjusting shape and material of the element, thereby realizing personal customization and suitable for operation requirement of different patients.

Thirdly, in the returnable and dynamic fixation pedicle screw system of rail-chain type for socket according to current invention, by engagement of the locating step and socket rail and restriction of the resilient filling element, spine segments activity ability of the patient after resilient fixation of the spine is able to be recovered and maintained. In addition, this system may also control excessive activity of the spine segments after patient operation.

DETAILED DESCRIPTION OF THE INVENTION

Various embodiments of the invention will be described below in further detail with reference to the accompanying drawings.

Figure 1:
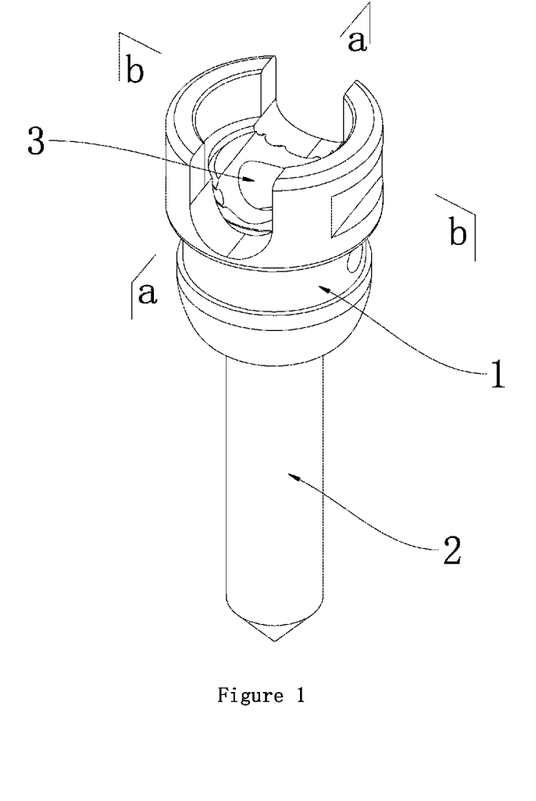
FIG. 1 shows a perspective view of a socket pedicle screw according to one embodiment of the invention.
Figure 2:
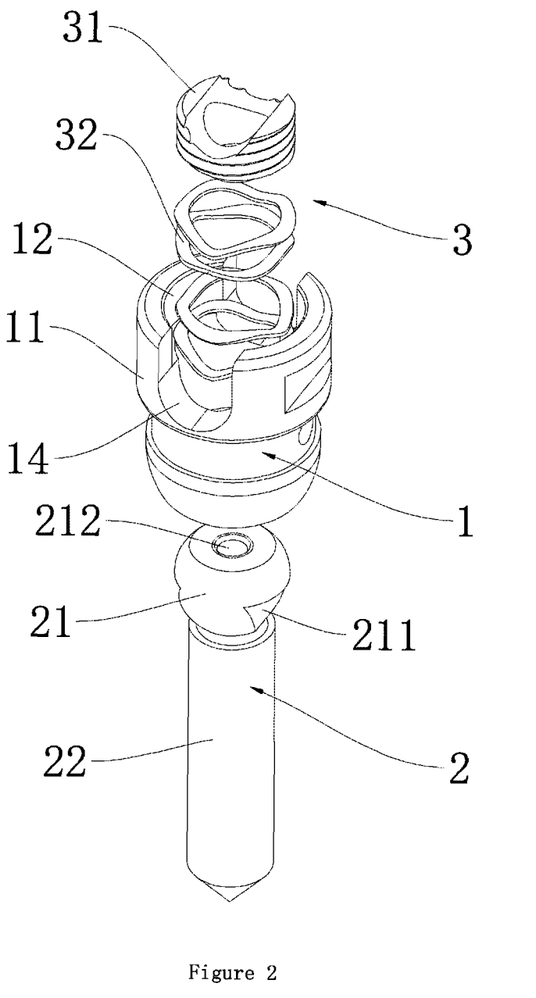
FIG. 2 shows an exploded perspective view of the structure of FIG. 1.
Figure 3:
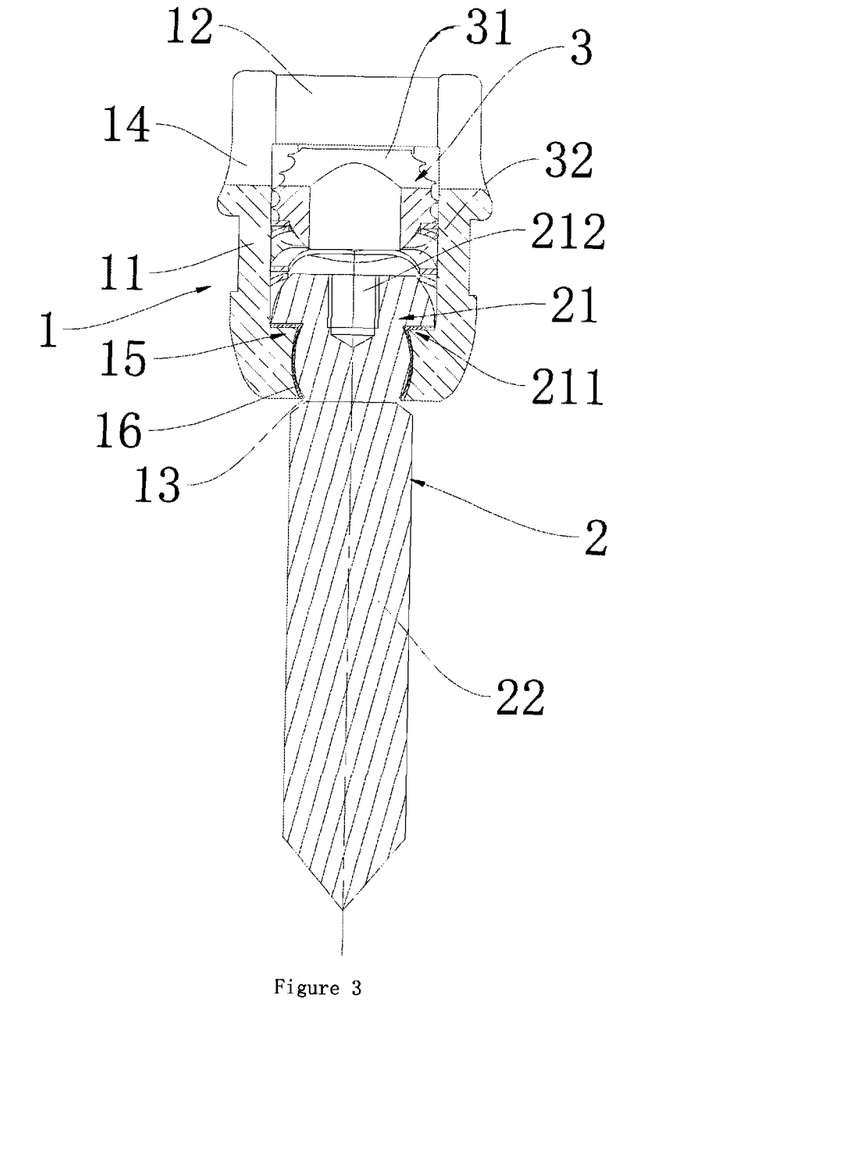
FIG. 3 shows a cross-sectional view of the structure of FIG. 1 along line a-a.

With reference to FIGS. 1-3, a socket pedicle screw according to one embodiment of the invention includes a fixator 1, a spherical head screw 2 pivotally disposed at a bottom of the fixator 1, a resilient filling element 3 disposed inside the fixator 1, and a retention screw cap (not shown) screwed to a top of the fixator 1 to be pressed against the spherical head screw 2.

With reference to FIGS. 2-6, the fixator 1 has a circular sidewall 11 and a though hole defined by the sidewall 11. The though hole includes a top opening 12 and a bottom opening 13. A pair of diametrically faced and U-shaped grooves 14 (See FIGS. 2 and 6) is defined downwardly from the edge of the top opening 12 and long the circular sidewall 11. A pair of locating steps 15 is internally extended from an inner wall of a portion, adjacent to the bottom opening 13, of the circular sidewall 11 and the pair of steps 15 is located below the pair of U-shaped grooves 14. In addition, each of the locating steps 15 is formed by a first top wall 151 and a first sidewall 152 collectively (See FIGS. 5-6).

Figure 7:
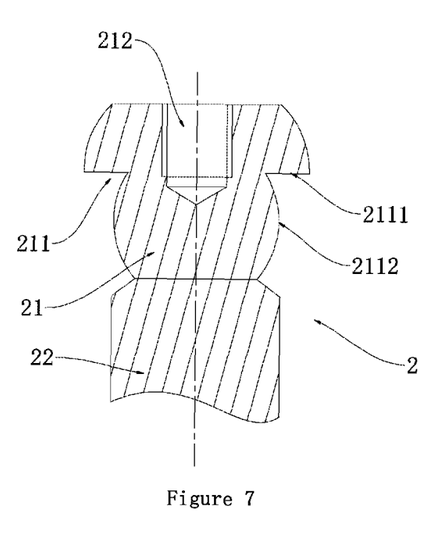
FIG. 7 shows an enlarged cross-sectional view of a spherical head screw of FIG. 3.

Please refer to FIGS. 2-4 and 7, the spherical head screw 2 includes a bolt 22 and a spherical head 21 disposed at the top portion of the bolt 22. A pair of socket rails 211 is formed on a lower portion of the head 21 and engages the pair of locating steps 15 respectively. Specifically, as shown in FIG. 7, the head 21 includes a body which is recessed to form a second top wall 2111 and a second sidewall 2112 downwardly extended to the bottom of the head 21. Each socket rail 211 is constructed collectively by the second top wall 2111 and a corresponding second sidewall 2112. Alternatively, the body of the head 21 may also be externally extended to form a second top wall and a second sidewall downwardly extended to the bottom of the head 21. Furthermore, a screw-removing hole 212 for assisting in removal of the spherical head screw may be defined in the top portion of the head 21.

Figure 5:
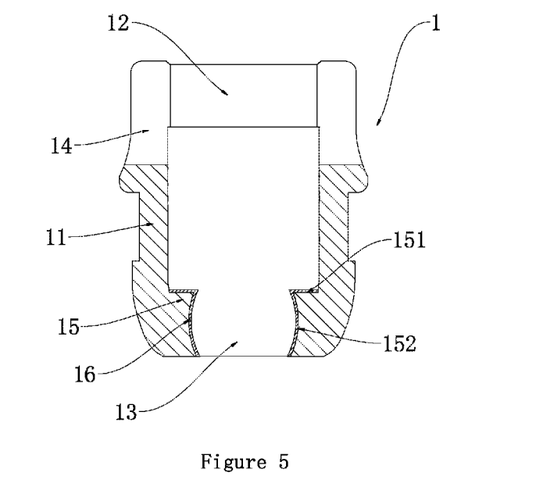
FIG. 5 shows an enlarged cross-sectional view of a fixator of FIG. 3.
Figure 6:
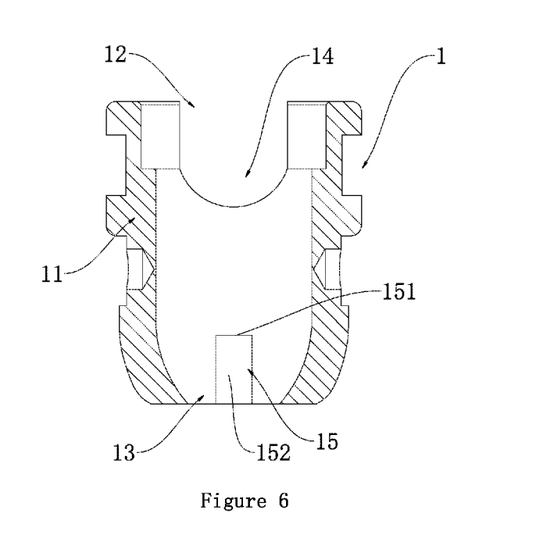
FIG. 6 shows an enlarged cross-sectional view of a fixator of FIG. 4.

Reference is further made to FIGS. 3, 5, and 7. The spherical head screw 2 is inserted from the top opening 12 of the fixator 1 such that the bolt 22 of the spherical head screw 2 passes out of the bottom opening 13, while the head 21 is secured into the fixator 1. Specifically, the second top wall 2111 of the socket rail 211 is vertically pressed against the first top wall 151 of a corresponding locating step 15. Furthermore, a gap is defined between the first sidewall 152 and second sidewall 2112. Preferably, an arced surface conforming to that of a spherical surface of the body of the head 21 is defined on the second sidewall 2112 of the socket rail 211. In addition, an arced surface conforming to that of the second sidewall 2112 is defined on the first sidewall 152 of the locating step 15. Here, the width of the first sidewall 152 is smaller than that of the second sidewall 2112. When the first and second sidewalls 152 and 2112 are pressed against each other, a rounded relative activity space is defined between the fixator 1 and spherical head screw 2. To reduce impact and friction loss between the locating step 15 and socket rail 211, a buffer layer 16 is disposed on both of the first top wall 151 and first sidewall 152 (See FIG. 5). Or, this buffer layer may also be disposed on both of the second top wall 2111 and second sidewall 2112 (not shown).

The returnable and dynamic fixation pedicle screw system of rail-chain type for socket of the invention includes a plurality of above-mentioned socket rail pedicle screws and a rectifying rod interconnecting these screws. The plurality of above-mentioned socket rail pedicle screws may be screwed into the disease focus of the spine of the patient and, relative locations of the screws are determined and maintained by the rectifying rod so as to facilitate recovery and fixation of the spine.

The rectifying rod connecting the plurality of above-mentioned socket rail pedicle screws is located into the pair of U-shaped grooves 14 of each socket rail pedicle screw. In addition, the retention screw cap screwed to the top of the fixator 1 is directly pressed against the rectifying rod. The returnable and dynamic fixation pedicle screw system of rail-chain type for socket of the invention further includes the resilient filling element 3 as described above and disposed in a space defined by the rectifying rod and spherical head screw 2.

Figure 4:
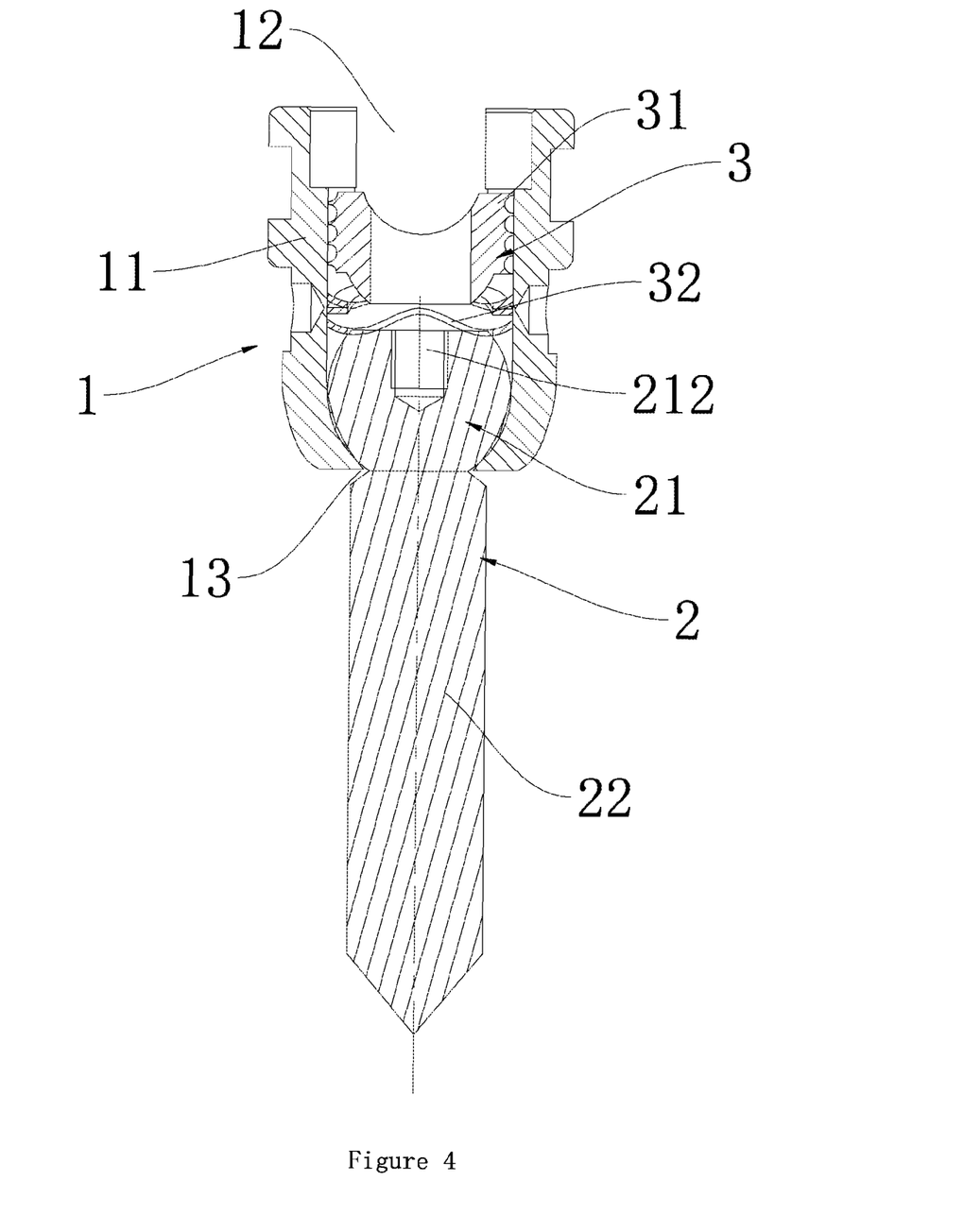
FIG. 4 shows a cross-sectional view of the structure of FIG. 1 along line b-b.

With reference to FIGS. 2-4, the resilient filling element 3 includes a supporting cushion 31 placed underneath the rectifying rod and an adjusting cushion 32 disposed above the head 21 of the spherical head screw 2.

In this embodiment, a notch for supporting the rectifying rod therein is defined in a top portion of the supporting cushion 31, and said notch communicates the U-shaped groove 14. Alternatively, the supporting cushion 31 may also be formed by a uniform resilient material and then a notch may be formed by bending or pressing the resilient material for supporting the rod. The adjusting cushion 32 is constructed by laminating a plurality of wave-shaped gaskets. Or, it may be constructed by a resilient post. To allow adjustment and freedom of activity of the spherical head screw 2, the adjusting cushion 32 has greater resiliency than the supporting cushion 31. The supporting cushion 31 may be integrally formed with the adjusting cushion 32.

Figure 8:
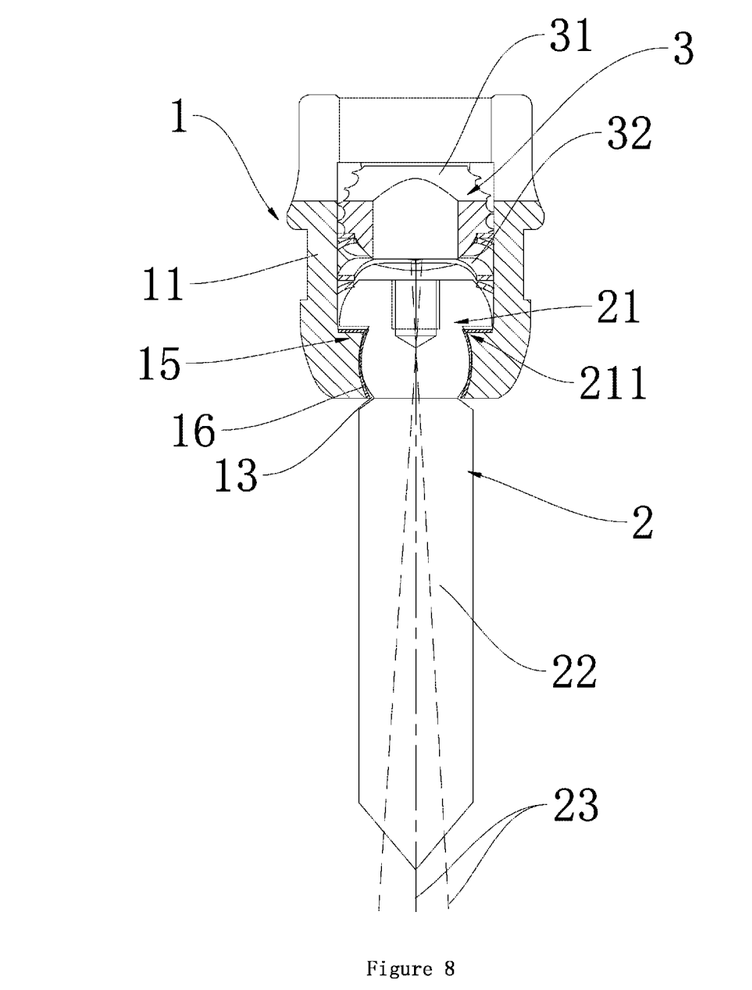
FIG. 8 illustrates movement range of a spherical head screw of the socket pedicle screw of the invention.

Referring to FIG. 8, thanks to engagement between the locating step 15 and socket rail 211, the spherical head screw 2 located below the fixator 1 is able to sway in an angular range (indicated by an axis 23 of the spherical head screw 2). Furthermore, freedom of swaying of the spherical head screw 2 is restricted by the resiliency of the resilient filling element 3 so as to better realize dynamic fixation effect of the returnable and dynamic fixation pedicle screw system of rail-chain type for socket of the current invention.

In a summary, the socket rail pedicle screw and returnable and dynamic fixation pedicle screw system of rail-chain type for socket of the invention have reasonable structure design, definite force distribution, stability, and are helpful to recovery of the patient after operation.

Though various embodiments of the invention have been illustrated above, a person of ordinary skill in the art will understand that, variations and improvements made upon the illustrative embodiments fall within the scope of the invention, and the scope of the invention is only limited by the accompanying claims and their equivalents.

The invention claimed is:

1. A socket rail pedicle screw, comprising a fixator, a spherical head screw pivotally disposed at a bottom of the fixator, and a retention screw cap pressed against the spherical head screw, wherein
   the fixator has a circular sidewall and a through hole defined by the circular sidewall, a pair of diametrically faced and U-shaped grooves is defined on a top portion of the circular sidewall, a pair of locating steps is internally extended from an inner wall of a bottom portion of the circular sidewall and the pair of locating steps is located below the pair of U-shaped grooves, and each of the locating steps is formed collectively by a first top wall and a first sidewall, having an arched surface, and extended from the first top wall;
   the spherical head screw includes a bolt and a spherical head disposed at a top portion of the bolt, a pair of diametrically faced socket rails is formed on a lower portion of the spherical head, and each socket rail is constructed collectively by a second top wall and a corresponding second sidewall, having an arched surface conforming to the arched surface of the first sidewall, and extended from the second top wall to a bottom of the spherical head;
   the second top wall is vertically pressed against the first top wall; and
   a gap is defined between the arched surface of the first sidewall and the arched surface of second sidewall.

2. The socket rail pedicle screw according to claim 1, wherein a width of the first sidewall is smaller than that of the second sidewall.

3. The socket rail pedicle screw according to claim 2, wherein the spherical head includes a body which is recessed to form the second top wall and the second sidewall.

4. The socket rail pedicle screw according to claim 2, wherein the spherical head includes a body which is externally extended to form the second top wall and the second sidewall.

5. The socket rail pedicle screw according to claim 3, wherein a buffer layer is disposed on both of the first top wall and first sidewall.

6. The socket rail pedicle screw according to claim 3, wherein a buffer layer is disposed on both of the second top wall and second sidewall.

7. The socket rail pedicle screw according to claim 1, wherein the socket rail pedicle screw further comprises a resilient filling element disposed inside the fixator.

8. A returnable and dynamic fixation pedicle screw system of rail-chain type for socket, comprising a plurality of socket rail pedicle screws as recited in claim 1 and a rectifying rod interconnecting the plurality of socket rail pedicle screws, said rectifying rod being located into the pair of diametrically faced and U-shaped grooves of each socket rail pedicle screw.

9. The returnable and dynamic fixation pedicle screw system of rail-chain type for socket according to claim 8, further comprising a resilient filling element disposed inside a corresponding socket rail pedicle screw, said resilient filling element including a supporting cushion placed underneath the rectifying rod and an adjusting cushion disposed above the spherical head of the spherical head screw.

10. The returnable and dynamic fixation pedicle screw system of rail-chain type for socket according to claim 9, wherein a notch is defined in the supporting cushion for axial engagement with the rectifying rod.

11. The returnable and dynamic fixation pedicle screw system of rail-chain type for socket according to claim 9, wherein the adjusting cushion is constructed by laminating a plurality of wave-shaped gaskets.

12. The returnable and dynamic fixation pedicle screw system of rail-chain type for socket according to claim 9, wherein the resilient filling element is integrally formed.

* * * * *